United States Patent [19]
Nettekoven

[11] Patent Number: 5,588,634
[45] Date of Patent: Dec. 31, 1996

[54] FLUID FLOW CONTROL DEVICE PINCH MECHANISM

[75] Inventor: William S. Nettekoven, Sandy, Utah

[73] Assignee: MegaDyne Medical Products, Inc., Draper, Utah

[21] Appl. No.: 570,641

[22] Filed: Dec. 11, 1995

[51] Int. Cl.⁶ ........................................................ F16K 7/06
[52] U.S. Cl. ................................................. 251/9; 251/263
[58] Field of Search ..................................... 251/4, 9, 233, 251/237, 243, 242, 251, 252, 253, 258, 260, 261, 263

[56] References Cited

U.S. PATENT DOCUMENTS

| | | |
|---|---|---|
| 790,353 | 5/1905 | Estlingen . |
| 2,624,364 | 1/1953 | Detlefsen . |
| 4,047,844 | 9/1977 | Robinson ................................. 251/9 X |
| 4,269,333 | 5/1981 | Nohai et al. ................................ 251/9 |
| 4,425,113 | 1/1984 | Bilstad . |
| 4,425,116 | 1/1984 | Bilstad . |
| 4,852,551 | 8/1989 | Opie . |
| 5,026,020 | 6/1991 | Betush ................................. 251/9 X |
| 5,195,959 | 3/1993 | Smith . |

*Primary Examiner*—John C. Fox
*Attorney, Agent, or Firm*—John L. Sigalos

[57] ABSTRACT

An improved pinch mechanism for a fluid flow control assembly. It comprises a trumpet-type actuator moveable along its principal axis to control flow through an associated resilient tubular member. Interconnected with the actuator is a caming assembly having a roller guide with a principal surface sloping at an acute angle with respect to the actuator principal axis. Engaging with that principal surface is a dog-leg shaped cam follower that is pivoted at one end for partial rotational movement about the pivot. It is spring loaded to normally retain it in a position in which a proximal end of the follower is pressed on a resilient surface of the tubular member to squeeze it closed. Partial rotation of the cam follower occurs when the actuator moves along its principal axis and the cam forces the cam follower to move through an arc that permits the squeezed tubular member to assume its normally unsqueezed and open shape.

16 Claims, 6 Drawing Sheets

FLUID FLOW CONTROL DEVICE PINCH MECHANISM

This invention relates to fluid flow control devices and more particularly to such devices that are specially adapted for use in performing medical procedures.

BACKGROUND OF THE INVENTION

As surgical knowledge and techniques have progressed, there has been a corresponding trend toward size reduction of surgical incisions and invasive instruments, thus decreasing patient trauma and contributing to rapidity of patient recovery. This has led to the practice of endoscopy including laparoscopic surgical procedures which are characterized by one or more very small incisions or openings as contrasted with the previously conventional large incisions. Since corrective procedures are conducted through very small incisions or other openings, it has become important to provide for multiple techniques/procedures to be performable by a single very small instrument. Examples of such multiple techniques/procedures include fluid flow control such as irrigation, suction and deployment of one or more surgical electrodes.

Recent discoveries of the danger of transmitting deadly diseases such as AIDS have led to heightened awareness of the importance of complete and thorough sterilization. Although it is possible to clean and sterilize suction-irrigation devices both exteriorly and interiorly, the cleaning and sterilization procedures have been time consuming and costly. Accordingly, there has been a need for continuing improvements in suction-irrigation devices that provide the needed multiple capabilities while being easily and quickly cleaned and prepared for re-use.

Multi-element suction-irrigation devices have heretofore been proposed, illustrative of which are those described in U.S. Pat. No. 790,353 granted to E. S. Estlingen on May 23, 1905; U.S. Pat. No. 2,624,364 granted to G. C. Detlefsen on Jan. 6, 1953; U.S. Pat. No. 4,425,113 granted to Arnold C. Bilstad on Jan. 10, 1984; U.S. Pat. No. 4,425,116 granted to Arnold C. Bilstad et al on Jan. 10, 1984; U.S. Pat. No. 4,852,551 granted to Erie A. Opie et al on Aug. 1, 1989; and U.S. Pat. No. 5,195,959 granted to Paul C. Smith on Mar. 23, 1993. Collectively, these patents disclose various forms of squeeze control, multi-passage conduits, disposable inserts, trumpet-type control valves and hinged housings. However, while these patents individually suggest various ones of the foregoing features, they do not singly or in combination teach or suggest a multi-passage suction-irrigation device that includes all of those features while being adapted for equally easy use in either the right or left hand of the user.

In co-pending U.S. patent application Ser. No. 08/312,479 filed Sept. 26, 1994, there is disclosed an improved suction-irrigation device that includes a hinged housing for ease of opening, a contoured interior adapted for receiving a disposable tri-tubular cassette that is discarded after each use, a plurality of improved trumpet type piston-operated plungers in combination with rollers and wedging surfaces to facilitate squeeze control of flow through the cassette tubes, and push/snap on-off cassette connections for connecting tubing to facilitate rapid deployment and re-deployment of the suction-irrigation device. Through the efficacious use of rollers, wedges and springs, improved flow control is achieved while enhancing the feel associated with operation and reducing required finger pressure.

While the proposals of the foregoing co-pending application offer substantial advantages over the prior art, the mechanisms employed have been found to require care in maintaining internal alignment of parts and to be susceptible to malfunction if subject to jarring impact. Accordingly, while such proposals are generally attractive and offer substantial improvements, there has nevertheless been a need for further improvements.

BRIEF SUMMARY OF THE INVENTION

The mechanisms according to the present invention embody a combination of cam, roller, compression spring and tubular member which, through interactive co-action, improve mechanical advantage, foster ease of assembly and contribute to reliability and shock resistance. In addition, they feature reduction in cost of components.

A dog-leg shaped member is pivoted at one end and an inexpensive compression type spring normally forces the remaining end to compress an engaging section of an associated tubular member to a shut-off condition. Operation of a trumpet-type actuator progressively cams the non-pivoted end into a disengaging relationship with the tubular member thus releasing the closing force imparted thereto and permitting the resilience of the tubular member to return the tubular member to its open condition.

OBJECTS AND FEATURES OF THE INVENTION

It is one general object of the invention to improve fluid control devices.

It is another object of the invention to reduce costs of such fluid control devices.

It is yet another object of the invention to improve mechanical advantage while controlling fluid flow through a fluid control device.

It is still another object of the invention to further reduce finger pressure required to control fluid flow through the fluid control device.

It is yet one additional object of the invention to increase shock resistance of fluid control devices.

In accordance with still another feature of the invention, a trumpet valve element is spring loaded with an inexpensive compression-type spring and fitted with a specially shaped cam and follower which moves into and out of engagement with a predetermined portion of a corresponding tubular member, thus improving mechanical advantage and reducing user fatigue.

These and other objects and features of the invention will be apparent from the following description, by way of example of a preferred embodiment, with reference to the drawing.

DESCRIPTION OF A PREFERRED EMBODIMENT

Before proceeding to a detailed description of a preferred embodiment of the invention, reference is made to the above-identified co-pending United States patent application the disclosure of which is herein incorporated by reference.

It will be recalled from reference to the referenced co-pending United States patent application that the tri-tubular disposable insert described therein is comprised of the three tubes which preferably are made of material which include flexible portions that may be pinched off by the associated mechanisms. While three tubes are depicted in that application, for simplicity and clarity of presentation, only one such tube is illustrated herein, it being understood that the principles hereof are applicable to multi-tubular configurations.

Figure 1:
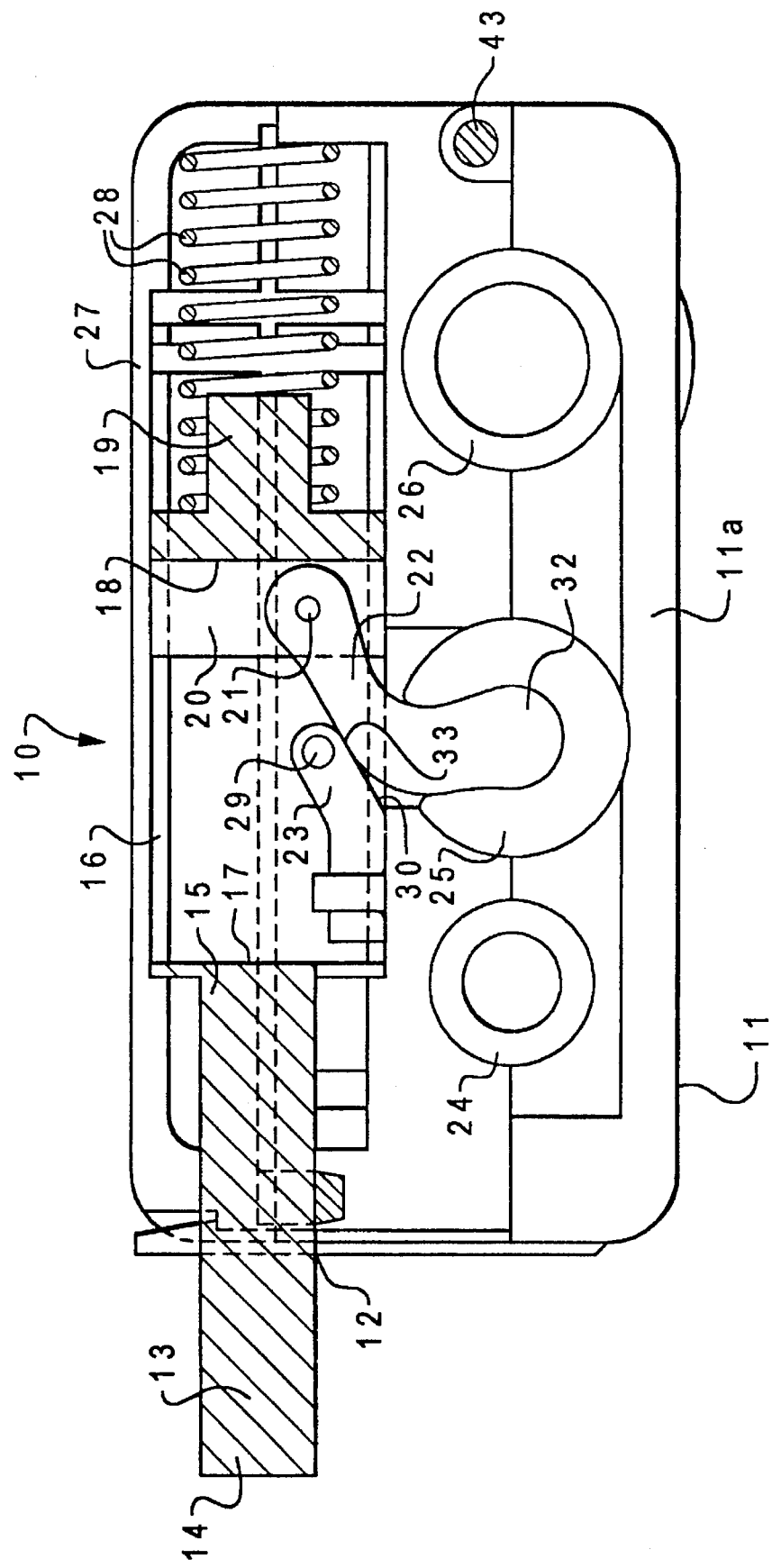
FIG. 1 is a sectional view through a suction irrigation device in a tube-closed condition and fitted with a mechanism constructed in accordance with the principles hereof.

Now turning to the drawing hereof, and more particularly FIG. 1, a sectional view is shown illustrating a suction-irrigation device 10 constructed in accordance with the principles hereof. As mentioned above, the mechanism of FIG. 1 is seen to be in a tube-closed condition. Illustrated there is conventional housing 11 having an aperture 12 through which trumpet valve actuator rod 13 projects from its proximal end 14 to its distal end 15. At distal end 15, there is affixed a longitudinal extension 16 that assures maintenance of the distance between enlarged face 17 and corresponding face 18. Thus, it will be evident that lateral movement of trumpet valve-type actuator rod 13 results in a corresponding lateral movement of member 19. The presence of swivel pin 43 should also be noted. It attaches the two parts of the housing 11 together and permits part 11a to swivel thereabout so as to open the housing for accessing the interior.

In fixed relationship to member 19 is a member 20 to which a cylindrical pivot 21 is affixed. Thus, progressive movement of actuator rod 13 (FIG. 2) results in a corresponding progressive movement of pivot 21. Mounted on pivot 21 and in swivelable relationship thereto is dog-legged shaped cam follower 22 which, due to its swivel mounting, is permitted to partially rotate through a limited arc about the axis of pivot 21.

Figure 2:
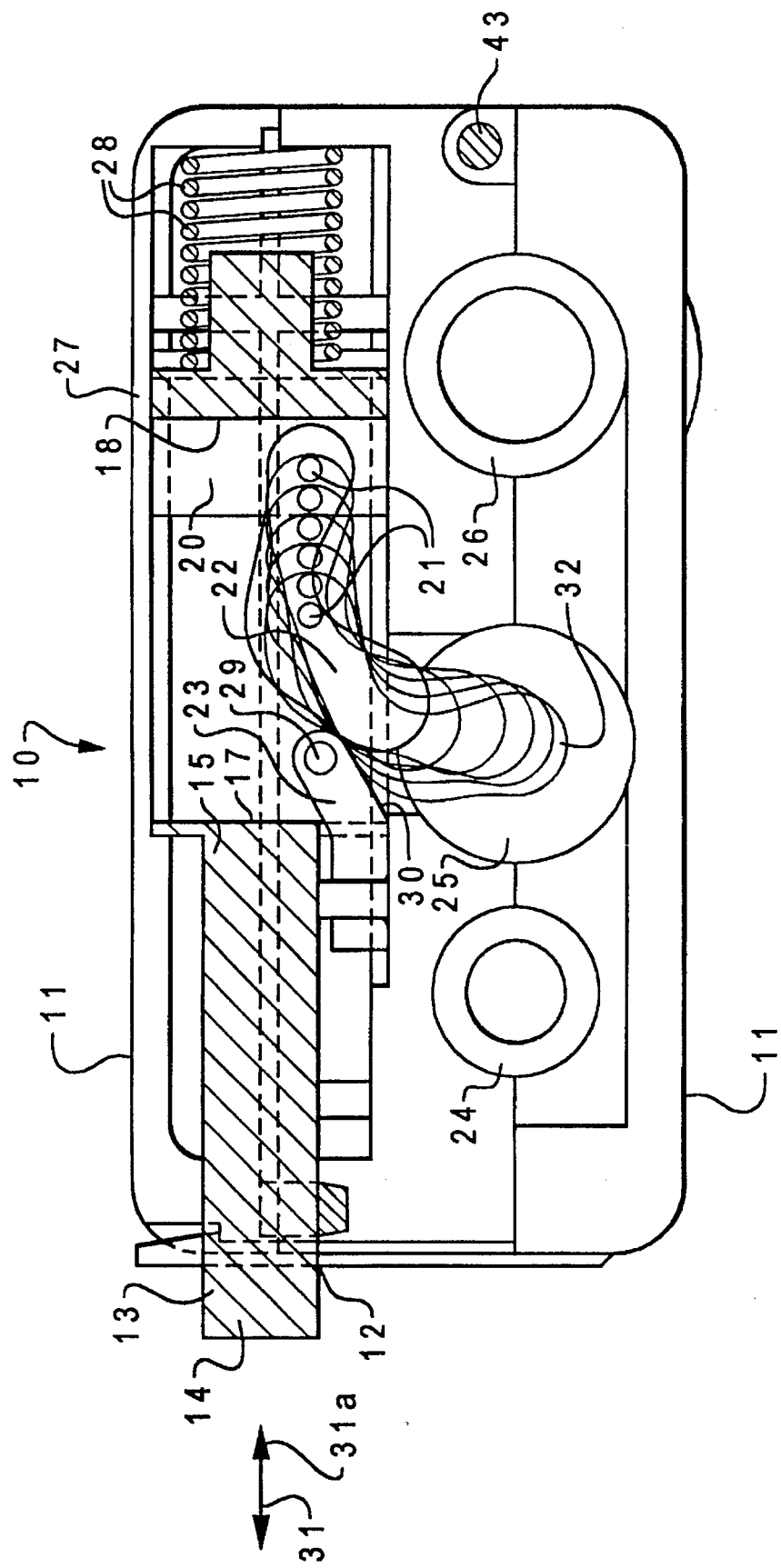
FIG. 2 is a sectional view similar to that of FIG. 1 and illustrating the progressive movement of the aforementioned camming assembly as a interconnected trumpet valve actuator is progressively depressed.
Figure 3:
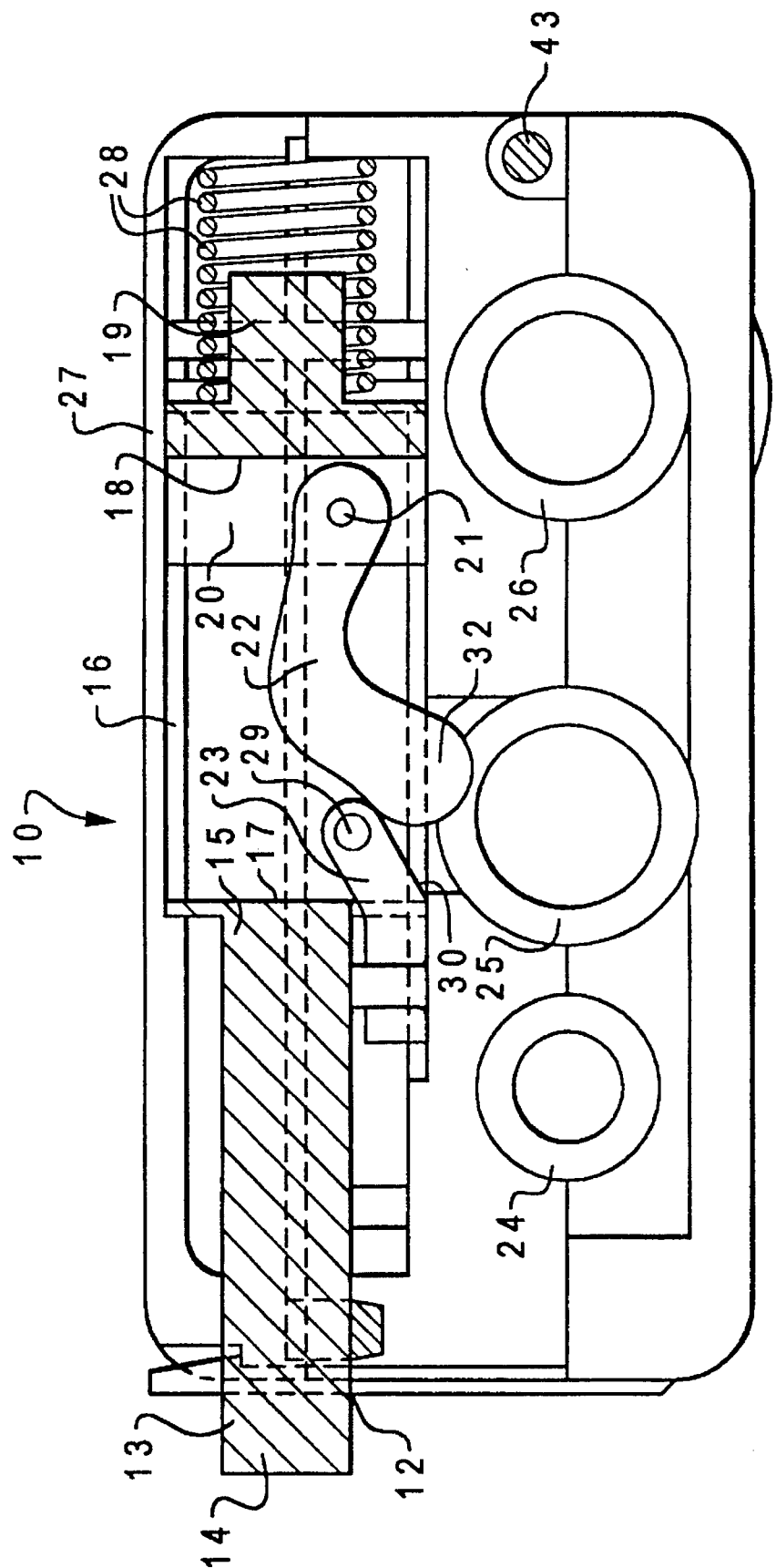
FIG. 3 is a sectional view similar to that of FIGS. 1 and 2 illustrating the condition of the camming assembly and associated tubular member when the trumpet valve actuator is in its fully depressed state.

Also shown in the figures are cam 23 and multiple fluid conducting tubular members 24, 25 and 26. The sections illustrated in FIGS. 1–3 are taken at a point at which the actuating mechanisms relating to tubular member 25 are disposed. However, it will be evident to those skilled in the art that to the rear of the illustrated sections is disposed a similar actuating mechanism for tubular member 24; and in front of the illustrated sections is disposed a similar actuating mechanism for the remaining tubular member 26. Of course, it will also be understood that the positions of tubular members 24 and 26 could readily be exchanged.

As described in the aforementioned co-pending United States patent application, the above-described mechanisms are preferably housed in a hinged cassette such as those shown in FIGS. 1–7 of the instant application. The exterior walls 27 of such case are made of any of a variety of conventional materials such as impact resistant plastic and the like. Also included within the cassette housing is an inexpensive and conventional compression spring 28.

It will be evident from further reference to FIG. 1 that spring 28 urges trumpet valve actuator rod 13 into a position in which it is most extended to the exterior of the cassette housing; and thus, since as described above its position determines the position of pivot 21, it normally imparts force through the intermediate parts of the mechanism, including dog-leg shaped cam follower 22, to deform the walls of resilient tubular member 25 to occlude the passageway therethrough and prevent liquid flow therein.

Before turning to FIG. 2, it is important to note the shape of dog-leg shaped follower 22 and roller guide 23. As employed in this specification and the appended claims the term "dog-leg" means a non-uniaxial elongated member having a rounded bend to form an obtuse angle in axial geometry generally similar to that of follower 22. It should also be noted that guide 23 includes a generally planar lower surface 30 which lies at an acute angle with respect to the central longitudinal axis of actuator rod 13.

Now considering FIG. 2, it will be seen to be similar to FIG. 1 except for depicting the change in position and orientation of cam follower 22 in response to depression of trumpet valve actuator rod 13 as denoted by double headed arrow 31. When the trumpet valve type actuator is depressed, rod 13 moves to the right as represented by right hand arrow head 31a. As this occurs, the above-described assembly of parts 15, 16, 19 and 20 correspondingly move to the right in FIG. 2; and, since pivot 21 is affixed to part 20, it moves correspondingly, carrying with it dog-leg shaped follower 22. As this occurs, the compressive forces present in the compressed and deformed resilient tubular member 25 push upward on end 32 with the result that end 32 moves progressively upwardly as shown to controllably release constrictive deformation of tube 25 and correspondingly permit fluid flow therethrough.

From further inspection of FIG. 2, the abovementioned camming action is observed. Thus, camming surface 33 of dog-leg shaped cam follower 22 is in continual contact with adjacent generally planar lower surface 30 and roller 29 of guide 23, thereby resulting in the above-described swiveling action of cam follower 22 about pivot pin 21. When actuator rod 13 is fully depressed, the above-described caming mechanism assumes the condition depicted in FIG. 3 in which end 32 of cam follower 22 is almost clear of tubular member 25 and consequently does not significantly restrict flow of fluid therethrough.

Figure 4:
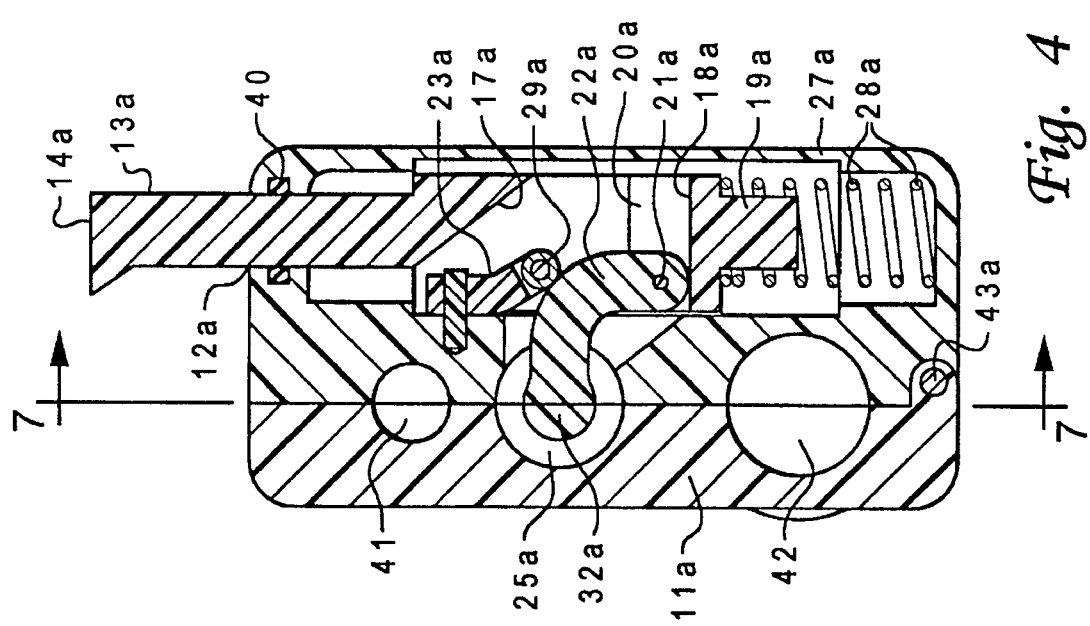
FIG. 4 is a sectional view through an alternate embodiment and generally corresponding to FIG. 1.

As mentioned above, FIG. 4 is a sectional view through an alternate embodiment and generally corresponds to FIG. 1. To facilitate description, it will be noted that similar elements are designated by the same numerals but with suffixes such as the letter "a". Thus, for example, in FIG. 4 the proximal end of the trumpet valve actuator rod is designated 14a, the actuator rod 13a, and the orifice through which the rod extends 12a. Most of the parts of FIG. 4 are like those of FIG. 1. However, as will be observed from an inspection, there are some differences. These include a combination guide/sealing member 40 and the depiction of passageways 41 and 42 without the presence of tubular members 24 and 26 therein. Other differences include the shape of surface 17/17a of distal end 15 of trumpet valve actuator rod 14/14a. In FIGS. 4–7 the surface 17a is inclined at an angle rather than parallel to surface 14a so as to conserve space and facilitate the desirable compact nature of the device.

Figure 5:
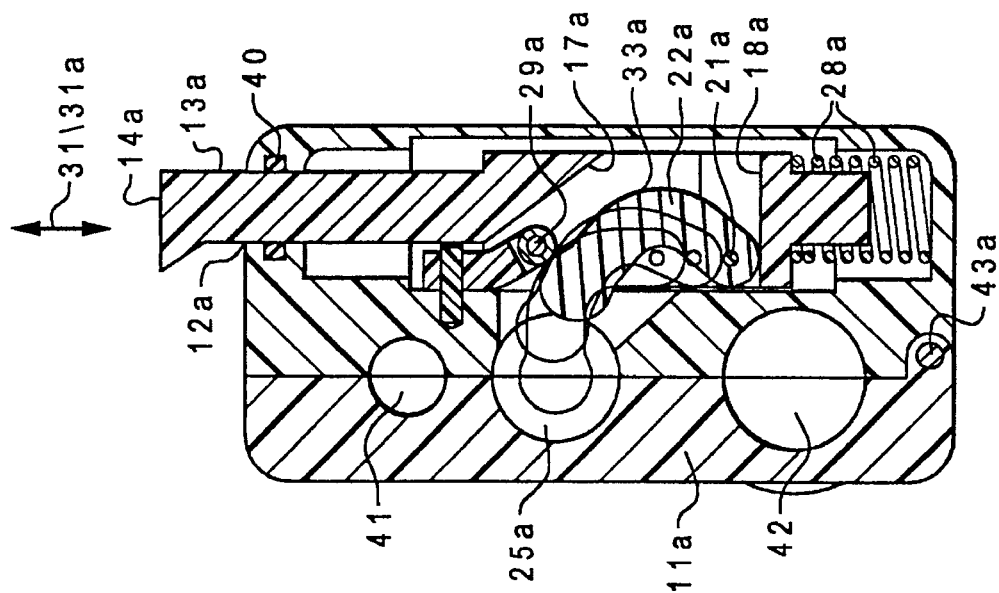
FIG. 5 is a sectional view through the alternate embodiment of FIG. 4 and generally corresponding to FIG. 2.

FIG. 5 is a sectional view through the alternate embodiment of FIG. 4 and generally corresponds to FIG. 2 except for the indicated differences.

Figure 6:
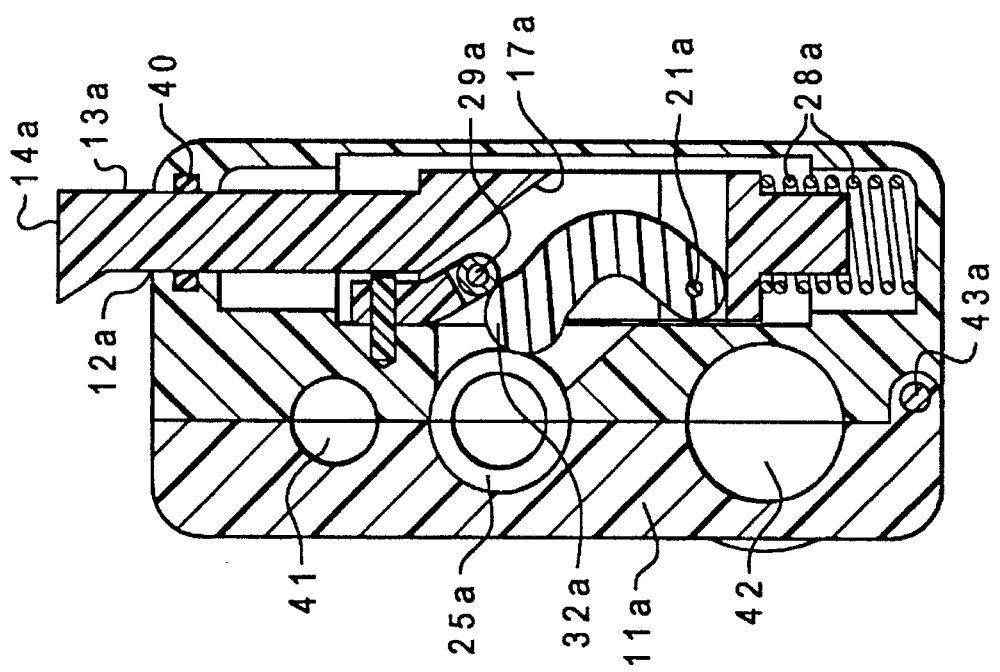
FIG. 6 is another sectional view through the alternate embodiment of FIGS. 4 and 5 and generally corresponding to FIG. 3.

FIG. 6 is another sectional view through the alternate embodiment of FIGS. 4 and 5 and, again, generally corresponds to FIG. 3 except for the foregoing differences.

Figure 7:
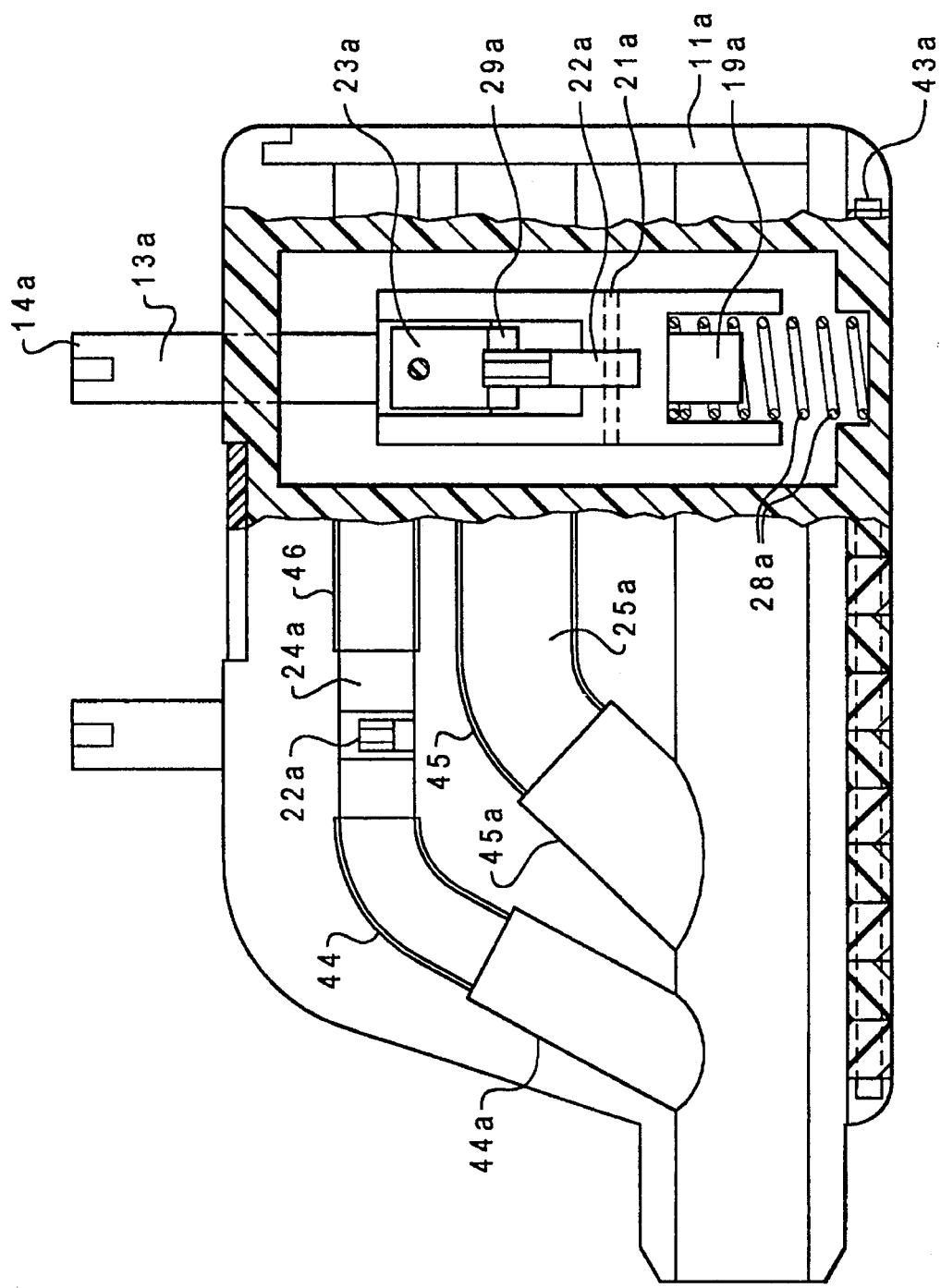
FIG. 7 is a side elevation of the embodiment of FIGS. 4–6 and with partial cut-away to expose details of the preferred trumpet valve in more detail.

FIG. 7 is a side elevation of the embodiment of FIGS. 4–6 and with partial cut-away to expose details of the preferred trumpet valve in more detail. There, it will be observed are shown elements including trumpet valve 13a, proximal end 14a, member 19a, cylindrical pivot 21a, dog-leg shaped cam follower 22a, cam 23a, resilient tubular members 24a and 25a, spring 28a, and hinge pin 43a about which the device cover 11 of housing 11 pivots to permit opening for accessing the interior. Also shown are channels 44, 44a, 45, 45a and 46 which are provided to receive and support resilient tubular members 24a and 25a.

It will now be evident that there has been described herein, a suction-irrigation device caming mechanism having improved control, feel, mechanical advantage and other handling qualities; that it is relatively simple and inexpensive in design, is relatively shock resistant, and that it is easy and cost-effective to produce and use, thus contributing to its attractiveness and desirability.

Although the invention hereof has been described by way of a preferred embodiment, it will be evident that other adaptations and modifications may be employed without departing from the spirit and scope thereof. Thus, for example, the principles of the invention may find expression in applications other than those appertaining to the medical field.

The terms and expressions employed herein have been used as terms of description and not of limitation; and thus, there is no intent of excluding equivalents, but on the contrary it is intended to cover any and all equivalents that may be employed without departing from the spirit and scope of the invention.

What is claimed is:

1. An improved flow control pinch mechanism comprising in combination:
   (a) a first fluid-conducting tubular member having an internal fluid conducting channel, said member having a resilient region capable of resilient deformation to controllably occlude said fluid conducting channel to control fluid flow therethrough;
   (b) a trumpet-type fluid control actuator having a spring-loaded piston;
   (c) a cam assembly for imparting fluid control force to said resilient region of said fluid conducting channel, said cam assembly comprising:
      (i) a cam having a principal camming surface,
      (ii) a cam follower engaging said cam and having a non-rectilinear principal axis with first and second ends lying at ends of said non-rectilinear principal axis, said cam follower having at said first end a pivot support for positioning said first end; and
   means including said trumpet-type fluid control actuator effective when said trumpet-type fluid control actuator is depressed for correspondingly causing relative movement between said cam and said cam follower to correspondingly cause said cam follower to pivot about said pivot support and correspondingly reduce said fluid control force.

2. A combination according to claim 1 further including a compression spring effective when said trumpet-type fluid control actuator is unactuated for imparting biasing force to said cam follower to urge said second end of said cam follower against said resilient region to constrict said fluid conducting channel.

3. A combination according to claim 2 wherein said biasing force occludes said fluid conducting channel.

4. A combination according to claim 1 wherein said principal camming surface of said cam is planar.

5. A combination according to claim 1 wherein said cam follower is dog-legged in geometrical configuration.

6. A combination according to claim 1 wherein said principal camming surface of said cam is planar.

7. A combination according to claim 6 wherein said trumpet actuator includes a principal axis of movement and wherein said principal caming surface of said cam is disposed at an acute angle with respect to said principal axis of movement of said trumpet actuator.

8. A combination according to claim 1 further including a housing enclosing said caming mechanism.

9. A combination according to claim 8 wherein said pivot support is disposed in fixed relationship to said actuator and wherein when said trumpet-type actuator is depressed, said cam follower moves as a linear function of movement of said actuator.

10. A combination according to claim 9 wherein said cam is rigidly connected to said housing.

11. A combination according to claim 1 further including:
   (a) an other fluid-conducting tubular member in fluid communication with said first fluid-conducting tubular member; and
   (b) a second trumpet-type fluid control actuator having a second spring-loaded piston in separate and exclusive camming relationship with said other fluid-conducting tubular member thereby to control flow of fluid through said other fluid-conducting tubular member.

12. A method of controlling fluid flow through a resiliently deformable fluid conducting tubular member comprising steps of:
   (a) providing a housing member;
   (b) positioning a resiliently deformable fluid conducting tubular member within said housing member;
   (c) disposing a moveable trumpet-type actuator in force imparting communication with said tubular member;
   (d) connecting a cam to said housing and a cam follower to said actuator to provide said force imparting communication;
   (e) disposing on said cam a principal caming surface at an acute angle with respect to axis of movement of said trumpet-type actuator;
   (f) pivotally connecting said cam follower to said actuator; and
   (g) moving said actuator to control force imparted to said tubular member.

13. The method of claim 12 further including a step of pivoting said cam follower in response to movement of said actuator.

14. The method of claim 12 further including a step of positioning said actuator partly within said housing.

15. The method of claim 13 further including a step of positioning said actuator partly within said housing.

16. The method of claim 12 further including a step of depressing said actuator to move said actuator.

\* \* \* \* \*